(12) United States Patent
Botos et al.

(10) Patent No.: US 7,038,334 B2
(45) Date of Patent: May 2, 2006

(54) HIGH PRECISION LASER MACHINING APPARATUS

(75) Inventors: Stephen J. Botos, Pittsburgh, PA (US); Brian P. O'Connor, Allison Park, PA (US)

(73) Assignee: Aerotech, Inc., Pittsburgh, PA (US)

( * ) Notice: Subject to any disclaimer, the term of this patent is extended or adjusted under 35 U.S.C. 154(b) by 0 days.

(21) Appl. No.: 11/069,213

(22) Filed: Mar. 1, 2005

(65) Prior Publication Data

US 2005/0236911 A1     Oct. 27, 2005

Related U.S. Application Data

(63) Continuation-in-part of application No. 10/830,979, filed on Apr. 23, 2004.

(51) Int. Cl.
 *B23K 26/10* (2006.01)
(52) U.S. Cl. .............................. 310/12; 355/72; 355/53
(58) Field of Classification Search ............ 219/67–69, 219/82, 84; 623/1.15; 29/896.6; 74/826
See application file for complete search history.

(56) References Cited

U.S. PATENT DOCUMENTS

| | | | |
|---|---|---|---|
| 5,346,345 A * | 9/1994 | Jerzycke et al. ............ 409/235 |
| 5,731,641 A | 3/1998 | Botos et al. ................... 310/12 |
| 5,759,192 A | 6/1998 | Saunders ..................... 606/194 |
| 6,323,935 B1 * | 11/2001 | Ebihara et al. ................ 355/53 |
| 6,356,219 B1 | 3/2002 | Weibel IV et al. .......... 341/120 |
| 6,511,504 B1 | 1/2003 | Lau et al. ................... 623/1.15 |
| 6,521,865 B1 | 2/2003 | Jones et al. ............ 219/121.72 |
| 6,588,081 B1 | 7/2003 | Botos et al. ................ 29/281.5 |
| 6,698,982 B1 * | 3/2004 | Watanabe et al. ........... 409/168 |

* cited by examiner

*Primary Examiner*—Karl Tamai
*Assistant Examiner*—Judson H. Jones
(74) *Attorney, Agent, or Firm*—The Webb Law Firm

(57) ABSTRACT

A high precision laser machining apparatus having a horizontal translation axis (z-axis) and a rotary axis (theta-axis) parallel with the translation axis comprises parallel spaced apart linear translation stages, a carriage supported between the parallel translation stages, and a rotation stage carried by the carriage between the parallel translation stages. Mounted on the same base plate is a laser optics support stage and a workpiece advance mechanism.

13 Claims, 8 Drawing Sheets

HIGH PRECISION LASER MACHINING APPARATUS

This is a continuation in part of application Ser. No. 10/830,979, filed Apr. 23, 2004.

BACKGROUND OF THE INVENTION

This patent relates to a high precision laser machining apparatus based on a z-theta stage. The stage has a horizontal translation axis (z-axis) and a rotary axis (theta-axis) parallel with the horizontal translation axis. The stage is especially designed for the manufacture of expandable stents for implantation in a human body or other cylindrical laser-machined components. The stents are manufactured from a tubular feedstock, such as stainless steel, nitanol, or plastic, and are provided with intricate circumferential patterns. Processes for machining the patterns out of the feedstock include laser machining in which a laser machining apparatus controlled by a CNC controller presents the feedstock to a laser beam for cutting away portions of the tubular feedstock. See U.S. Pat. No. 6,511,504 entitled "Expandable Stents and Method for Making Same" for a description of one stent manufacturing process; U.S. Pat. No. 5,759,192 entitled "Method and Apparatus for Direct Laser Cutting of Metal Stents"; and U.S. Pat. No. 6,521,865 entitled "Pulsed Fiber Laser Cutting System for Medical Implants".

SUMMARY OF THE INVENTION

Briefly, according to this invention, a high precision laser machining apparatus based on a z-theta stage has a horizontal translation axis (z-axis) and a rotary axis (theta-axis) parallel with the translation axis. The z-theta stage comprises a base plate having an upper surface lying in a plane and parallel spaced apart linear translation stages each having parallel linear bearings with bearing surfaces mounted at a substantially equal distance from the planar surface of the base plate. Each linear translation stage has a brushless linear motor. A carriage is supported between the parallel translation stages by the linear bearings. A rotation stage is housed in the carriage between the parallel translation stages, the rotation stage comprises a brushless rotating motor having a hollow shaft or rotor journaled with an axis parallel to the linear bearings. The carriage and rotation stage together have a vertical and a horizontal center of gravity. Each brushless linear motor is connected to the carriage by applying translation forces in a horizontal plane intersecting the vertical center of gravity of the carriage.

Mounted on the base plate to one side of the theta-axis is a positionable laser optics support. The positionable laser optics support comprises a centering stage for moving along an axis perpendicular to a given line intersecting the theta-axis. Carried by the centering stage is a focusing stage for moving toward and away from the theta-axis parallel to the given line intersecting the theta-axis. In a preferred embodiment, the centering stage moves along a tangent to a given circle included in a plane perpendicular to the theta-axis with its center at the theta-axis and the focusing stage moves toward and away from the theta-axis in a direction parallel to the radius of the given circle included in the plane perpendicular to the theta-axis with its center at the theta-axis. Typically, the theta-axis will be horizontal, in which event the centering stage will move vertically and the focusing stage will move toward and away from the theta-axis along a line parallel to a line intersecting the theta-axis and included in a vertical plane. The laser focusing optics are carried by the focusing stage. Because the centering stage and the linear translation stages are mounted on the same base plate, vibration introduced by the dynamics of the system of the base plate will not change the relative positions of the laser optics and laser beam and the workpiece.

Mounted on the base plate in line with the rotary axis is a workpiece advance mechanism that alternately slideably guides or grips the workpiece.

A linear position feedback device comprising a resolver, a laser interferometer, or an encoder may be associated with one or more of the brushless linear motors. A rotary feedback device comprising a resolver or encoder may be associated with the brushless rotating motor.

The laser machining apparatus may have fluid-actuated, workpiece-holding chucks attached to the rotor and the workpiece advance mechanism.

The rotor or shaft is preferably hollow to permit a cylindrical workpiece and/or a fluid-cooling jacket to be advanced therethrough or positioned therein.

Most preferably, the workpiece advance mechanism is arranged to support brackets guiding, grasping, and feeding a workpiece along the axis of the rotor.

According to another alternate embodiment, the precision z-theta stage has a carriage supporting two or more side-by-side identical rotation stages.

Preferably, the horizontal center of gravity of the carriage and rotary stage is located halfway between each linear motor.

Preferably, each linear stage contains a linear motion guide, cross roller, or air bearing.

Preferably, each linear motor is connected to the carriage at multiple locations spaced in the direction of linear translation.

BRIEF DESCRIPTION OF THE DRAWINGS

Further features and other objects and advantages will become clear from the following detailed description made with reference to the drawings in which.

DESCRIPTION OF THE PREFERRED EMBODIMENTS

Figure 1:
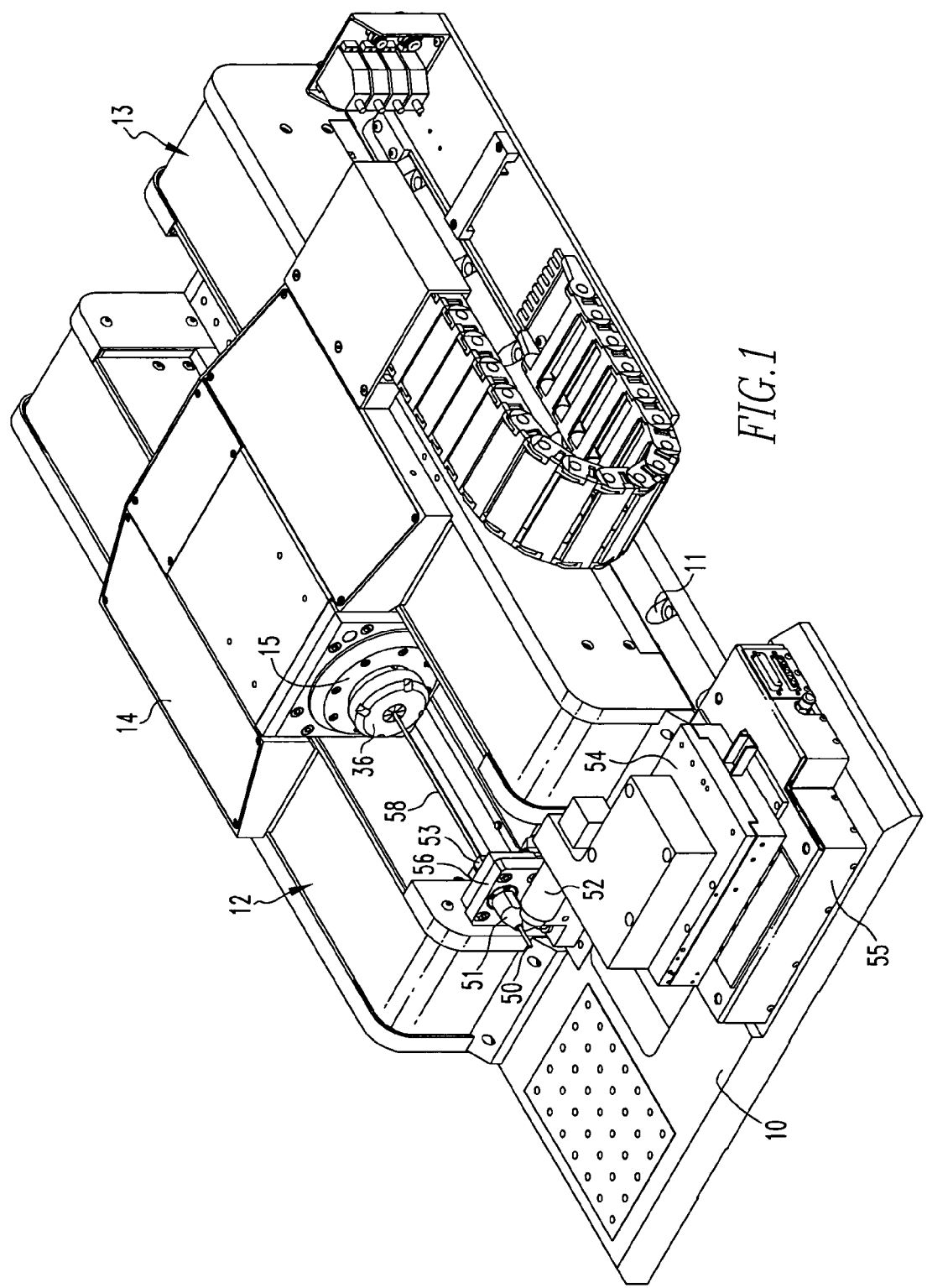
FIG. 1 is a perspective view of a laser machining apparatus according to this invention having a single rotary stage.

Referring to FIG. 1, there is shown a laser machining apparatus based on a z-theta stage suitable for manufacture of precision parts, such as stents. The apparatus includes a base plate 10 which is provided with openings 11 to receive bolts for securing the stage to a foundation which is usually a large piece of granite, casting, or welded structure. The base plate 10 is fabricated from metal, steel, or aluminum, for example. Mounted to the base plate are two parallel linear motor assemblies 12 and 13. Mounted between the linear motors and carried by them is a carriage 14 which supports a rotary motor 15 having an axis parallel to the translation axes of the linear motors. Preferably, the z-axis is horizontal or substantially horizontal. The linear motor assemblies and their support bearings define the z-axis and the rotary motor the theta-axis of the z-theta stage. An essential feature of this invention is that the linear motors are connected to the carriage to apply translation forces to the carriage directed along the surface of a plane that includes the vertical center of gravity of the carriage or passes as close to the vertical center of gravity as mechanically possible. In this way, the angular displacement between the axis of rotation of the rotary motor and the z-axis plane during a period of rocking following a translation movement is substantially eliminated. Practically speaking, the plane along which the translation forces are applied passes within 1 mm of the vertical center of gravity of the carriage. The axis of rotation of the rotary motor may hang somewhat below the plane upon which translation forces are applied.

Figure 2:
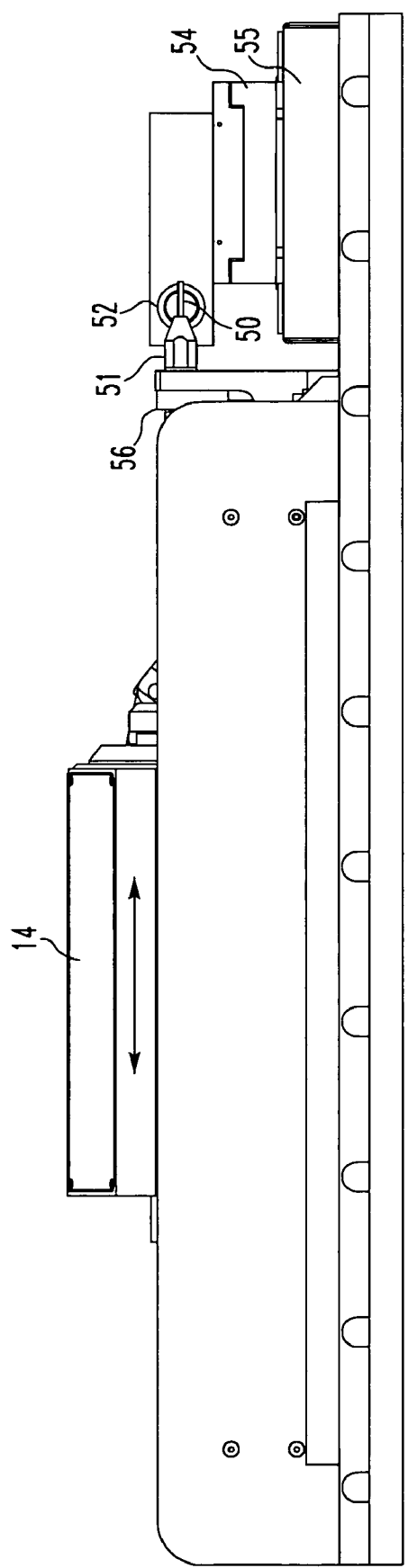
FIG. 2 is a side view of the laser machining apparatus according to FIG. 1.
Figure 3:
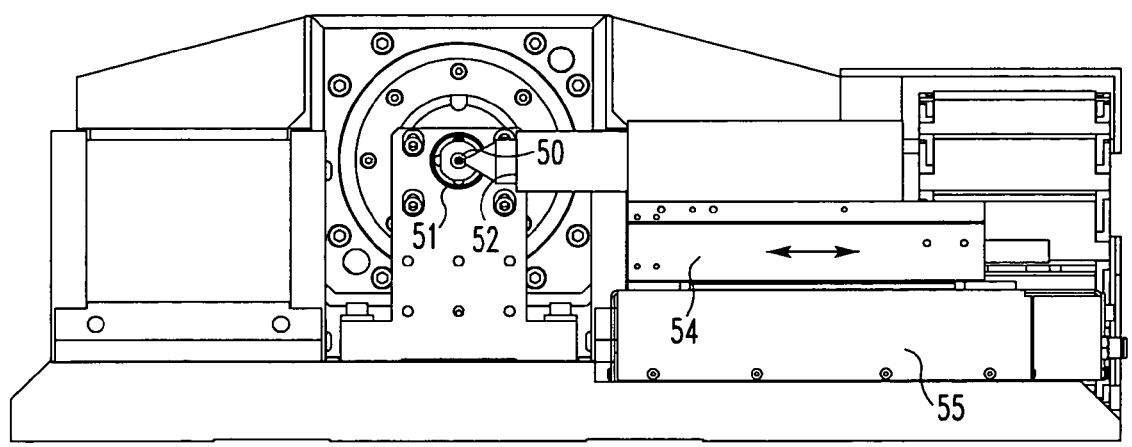
FIG. 3 is an end view of the laser machining apparatus according to FIG. 1.

Referring to FIGS. 1, 2, and 3, the laser machining apparatus is based upon a z-theta stage as more fully described with reference to FIGS. 4 to 8. The workpiece comprises a tube stock 58 that is fed along the hollow shaft or rotor of the rotary motor 15. During machining, the tube stock is clamped by collet chuck 36 associated with the rotor and is slideably guided by the tube support bushing 51 held in the tube advancing mechanism 56. The tube advancing mechanism includes a releasable tube stock gripper 53. The extension of the tube stock 58 beyond the tube support bushing comprises the workpiece 50 subjected to laser machining. When the laser machining of the workpiece 50, for example, into an expandable stent, is completed and the workpiece is cut from the tube stock, the carriage 14 is advanced to expose a new workpiece beyond the tube support bushing. Then the tube stock is clamped by the tube stock gripper 53 and the collet chuck 36 is released while the carriage retreats from the workpiece. Finally, the collet chuck 36 is again clamped and the tube stock gripper is unclamped.

Mounted on the base plate 10 is a laser optics support stage comprising a centering stage 55 which may comprise a vertical lift stage 55 to enable the alignment of the laser optics 52 with the workpiece. The centering stage may, for example, be a stage such as disclosed in U.S. Pat. No. 5,731,641 entitled "Linear Motor Driven Vertical Lift Stage". Mounted on the centering stage is a focusing stage 54 for advancing and retracting the laser optics toward and away from the workpiece. The focusing stage 54 may, for example, be a stage such as disclosed in U.S. Pat. No. 6,588,081 entitled "Small Footprint Direct Drive Mechanical Positioning Stage". The laser optics are typically lenses at the end of flexible fiber optic strands that are energized by a solid state laser, such as a Nd:YAG laser or fiber laser. An example of laser optics might be a first achromat lens for collating the laser beam and a second achromat lens for refocusing to give a very small spot diameter, say, about 8 microns. Optionally, associated with the laser optics may be a nozzle to deliver gas to assist the machining process.

Figure 4:
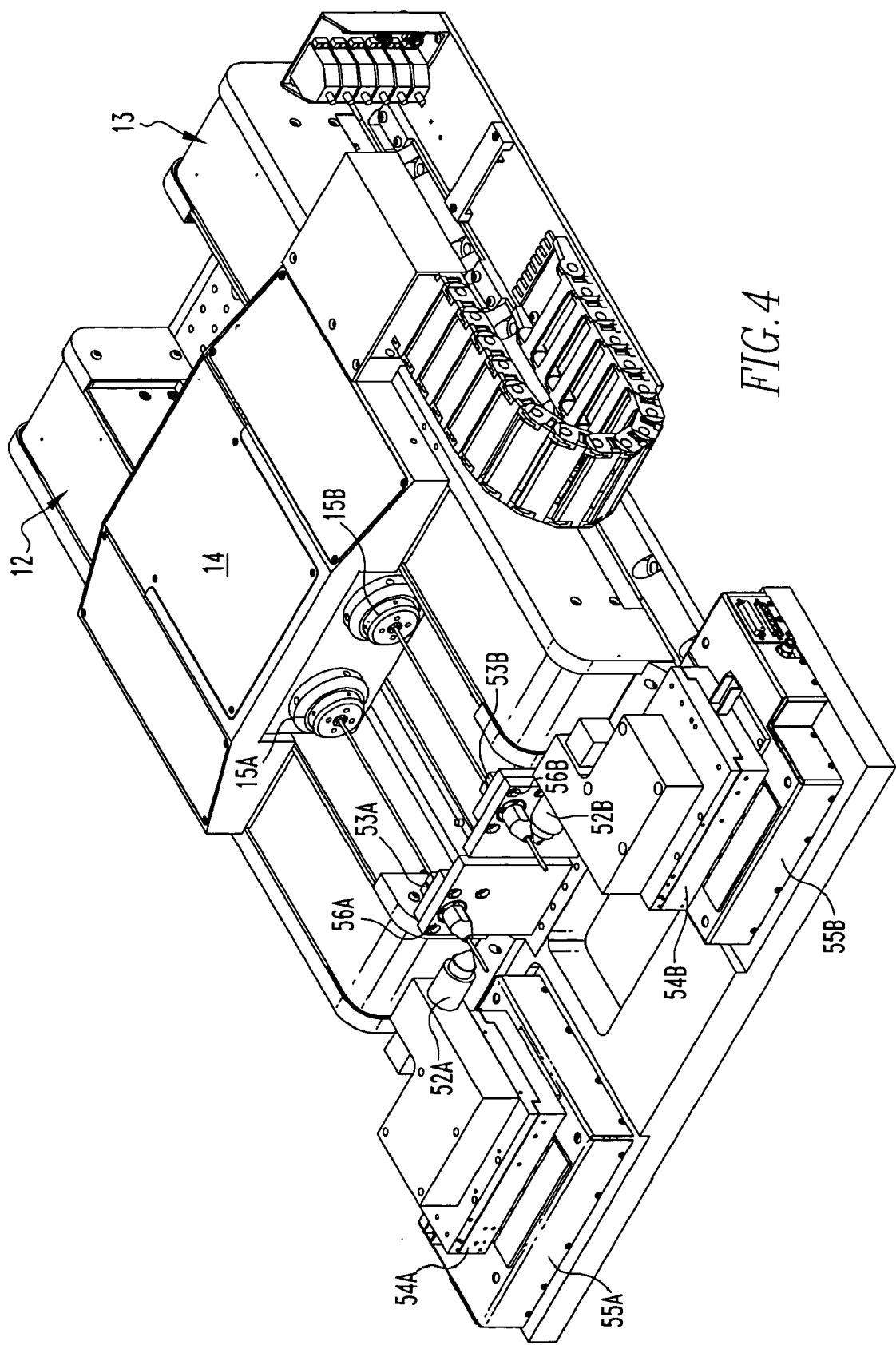
FIG. 4 is a perspective view of a z-theta stage according to this invention having a dual rotary stage.
Figure 5:
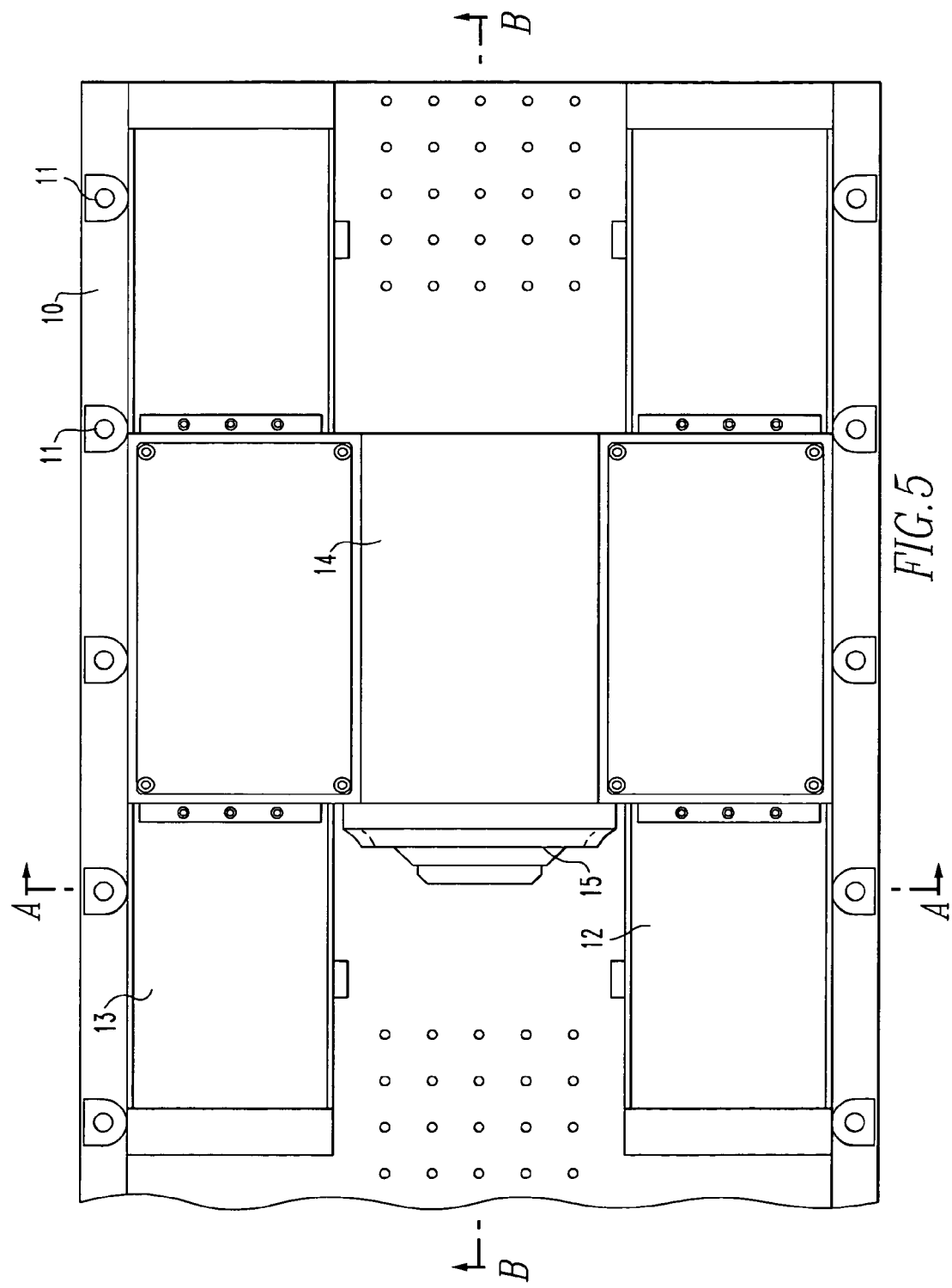
FIG. 5 is a plan view of the z-theta stage portion of FIG. 1.

FIG. 4 illustrates a variation of the z-theta stage shown in FIG. 1 in which dual theta stages (rotary motors 15A and 15B) are arranged side by side having parallel axes. Tube advancing mechanisms 56A and 56B and positionable laser optics are associated with each of the dual theta stages. Dual positioning stages (54A, 55A, 54B, and 55B) support dual laser optics 52A, 52B. The positionable laser optics supports would be mounted to the base opposite each other outside of both theta axes. It would be possible to process two workpieces simultaneously with this arrangement. In FIG. 4, identical elements are given identical numbers to those given for FIGS. 5 to 8.

The linear motors of the linear motor assemblies 12 and 13 are preferably permanent magnet linear motors, for example, direct drive brushless linear motors consisting of a noncontacting forcer coil 24 and a U-channel rare-earth magnet track 22. This design eliminates backlash, windup, wear, and maintenance associated with ball screws. Motors of this type are available from, among others, Aerotech, Inc. of Pittsburgh, Pa.

The rotary motor 15 is preferably a rotary brushless rare-earth magnet servomotor. It forms the basis of a direct drive theta stage. Preferably, the rotating shaft has an axial bore and is provided with an air-operated collet chuck. A motor of this type is available from Aerotech, Inc. of Pittsburgh, Pa.

Figure 6:
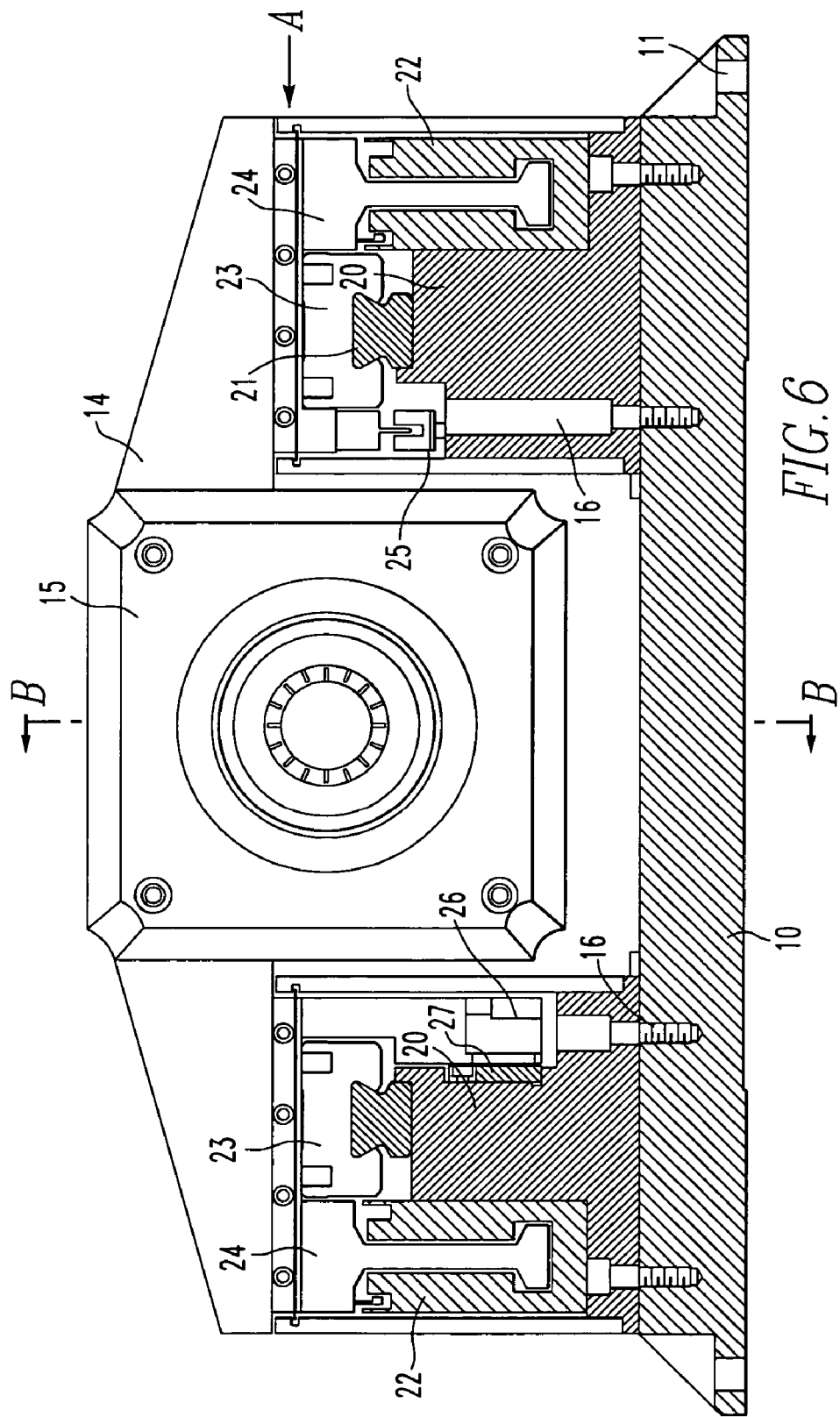
FIG. 6 is a section view along line A—A on FIG. 5 which is taken perpendicular to the theta-axis.

Referring now to FIG. 6, the linear motor comprise magnet track and forcer 22 and 24 are shown spaced apart, parallel, and positioned on the base plate 10. Associated with the motors are linear motion guides or bearings which may have, for example, cross roller bearings or air bearings. The rotary motor 15 is spaced with an equal distance between itself and the linear motors and with a rotating axis parallel to the linear motors.

Figure 8:
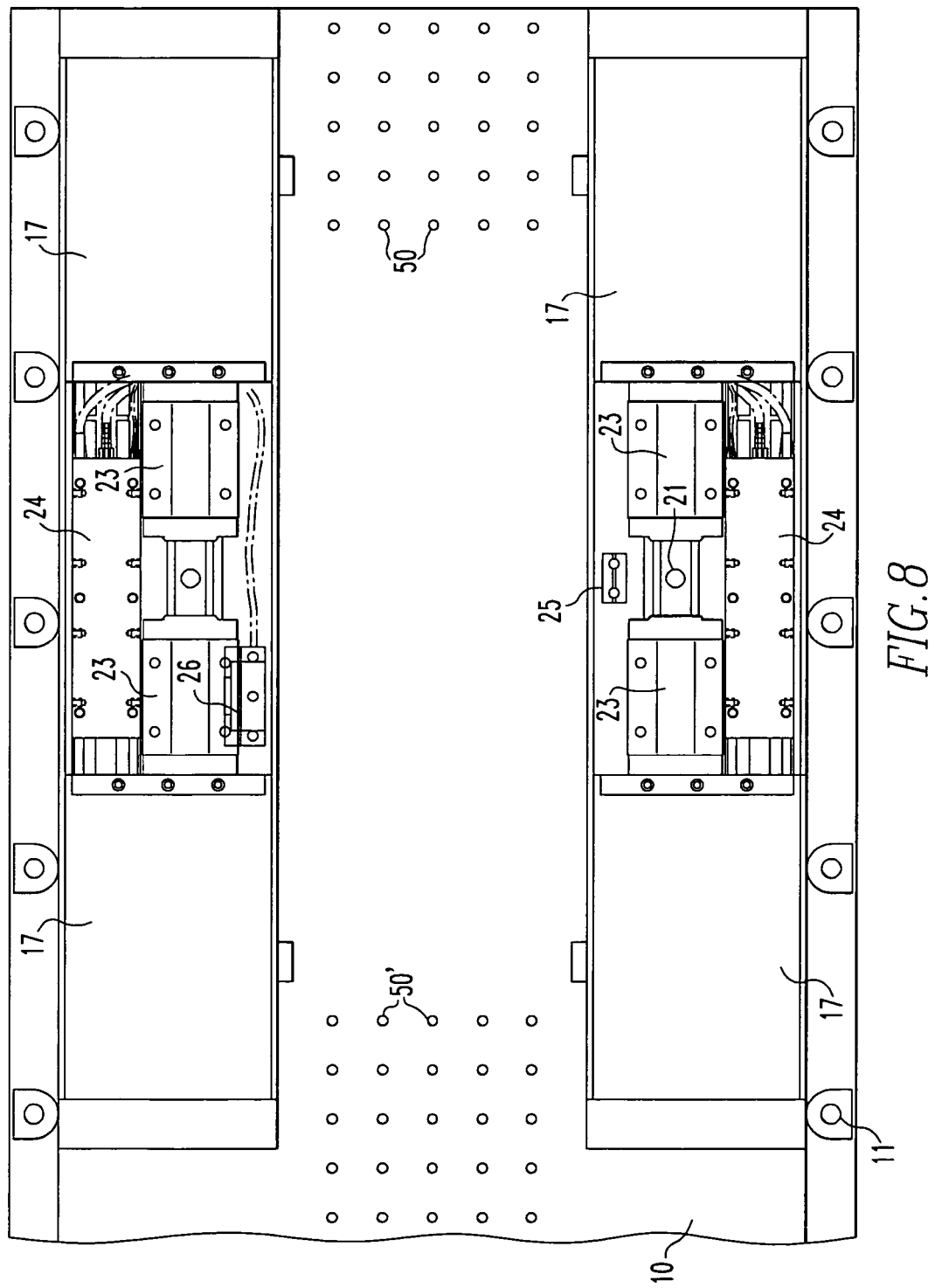
FIG. 8 is a plan view of the z-theta stage portion of FIG. 1 with the carriage removed.

Referring to FIG. 6, the linear motors are comprised of a linear spar 20 that is bolted the base plate 10 by bolts 16. The linear spar supports the track 21 of the linear bearing and the U-shaped magnet track 22. The magnet track 22 is a U-shaped channel fabricated from magnetic steel. It supports the rare-earth permanent magnets (not illustrated) arranged with alternating North and South poles facing inward at the forcer windings 24 along the length of the magnet track. The forcer windings are comprised of nonmagnetic materials so as not to be attracted by the magnet track 22. Bearing trucks 23 ride on the tracks 21 of the linear bearings and support the carriage 14. The forcer windings 24 are also secured to the carriage 14. As shown in FIGS. 6 and 8, the linear motor on the right side has a limit switch 25 associated therewith and the linear motor on the left side has an encoder read head 26 and encoder scale 27 associated therewith. As can be seen from FIG. 5, the linear motor applies translation forces to the carriage where the forcers are attached to the carriage (see arrow A in FIG. 6).

Attached to the carriage 14 and sliding over the linear motor assemblies 12 and 13 is a flexible sliding cover 17. The cover 17 slides over rollers 18 (see FIG. 7) guided downward at each end of the linear motors.

Figure 7:
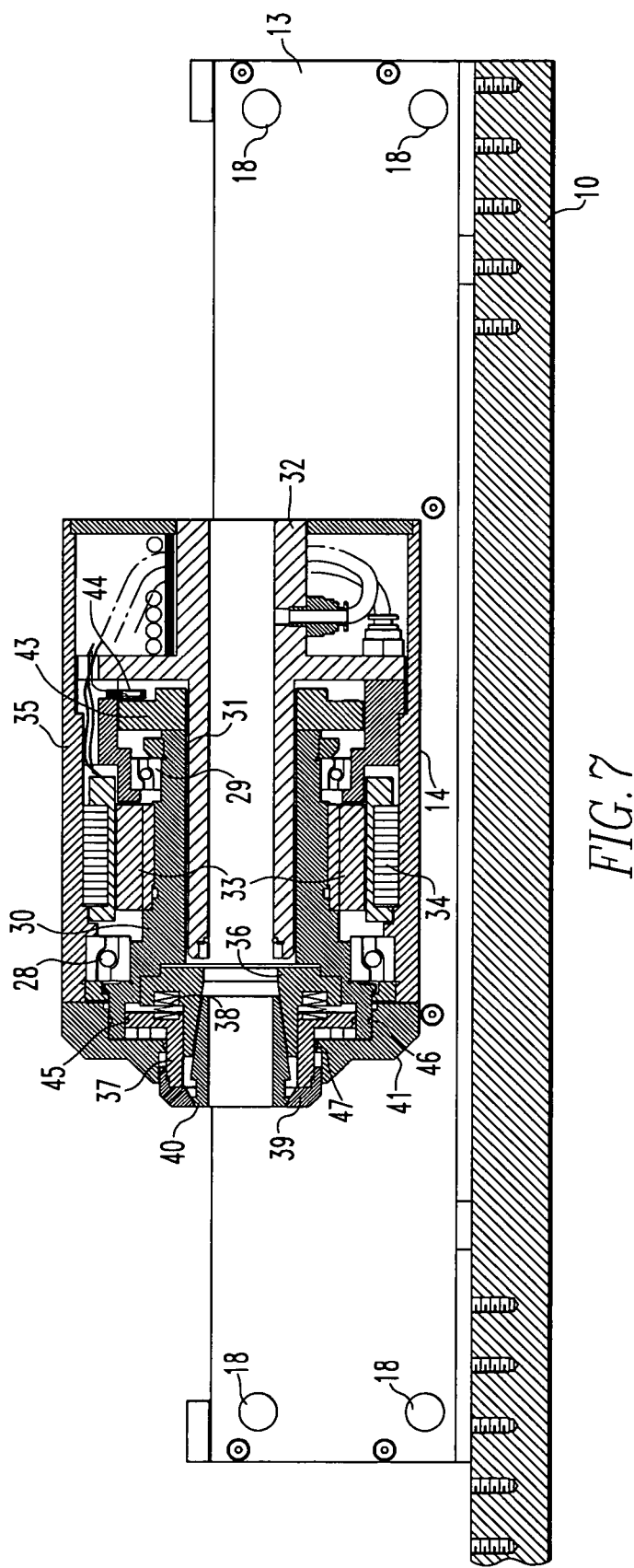
FIG. 7 is a section view along line B—B on FIGS. 5 and 6 which is taken along the theta-axis.

Referring to FIG. 7, the rotary motor 15 carried by the carriage 14 will now be described. Bearings 28 and 29 support rotating shaft 30 from an armature case 35 that is integral with the carriage 14. Armature windings 34 are secured to the armature case 35 in a typical manner. The windings may be supported by a laminated magnetic core with slots for receiving the windings or the windings may not be supported by a core with slots (i.e., slotless). Permanent magnets 33 are secured to the outer cylindrical surface of the shaft 30 in a typical manner. A rotary encoder scale 43 is attached to the shaft. A rotary encoder read head 44 is fixed with respect to armature casing 35.

According to one particularly advantageous embodiment, the armature winding is slotless and the shaft is made of aluminum or another lightweight metal. While the torque/ inertia ratio for this embodiment is low, the absence of cogging due to the slotless winding results in a superb theta stage for the manufacture of stents.

The shaft has a bore 31 extending end to end. In a particularly advantageous embodiment, nested within the bore 31 is a water jacket assembly 32 for cooling the shaft and a workpiece held in the shaft.

The bore 31 of the shaft 30 stepwise widens at one end to form two cylindrical seats, one having a larger diameter than the other. A tapered collet chuck 36 is fixed in the cylindrical seat of lesser diameter. A piston 37 rides within the seat of larger diameter and is telescoped over the tapered collet chuck 36. The piston 37 is biased by spring 38 towards the tapered collet chuck 36. Threaded to the piston is an annular threaded retaining cap 39 that has a tapered inner rim. A collet 40 is positioned to slide within the tapered collet chuck 36 and is held in place by the tapered inner rim of the retaining cap 39. According to one preferred embodiment, the collet 40 is of the ER-16 series available in multiple sizes from 0.05 mm to 10 mm. An annular manifold 41 is secured to the armature case 35. A piston chamber is formed between the manifold 41, the piston 37, and the larger diameter seat. Seals 45, 46, 47 are provided between the piston and the large diameter seat, between the shaft and the manifold, and between the manifold and the piston, respectively. A passage (not shown) is in communication with the piston chamber and a fitting is provided on the outside of the manifold 41 for supplying pressurized air to the piston chamber to force the piston over the collet to tighten the collet onto a workpiece (not shown). In this embodiment, the air pressure engages the collet with the workpiece; however, the piston can be arranged such that air pressure would release the collet.

The base plate 10 has at least one auxiliary tooling platform 50, 50' (see FIG. 8) arranged to support brackets guiding, grasping, and feeding a workpiece along the axis of the rotor.

The linear motors and rotary motor have associated position feedback means. In the specific embodiment described herein, position feedback is supplied from encoders. However, other position feedback means include resolvers and laser interferometers.

Incremental encoders are commonly used measurement transducers. Optical incremental encoders pass light from a lamp or light-emitting diode at a grating attached to the axis to be measured. The grating normally has two tracks offset 90 degrees apart with respect to each other (in quadrature). A single marker on a third track serves as a home marker (in the case of a rotary encoder, a one-per-revolution marker). The light reflected from the grating continues through a reticule or mask which, together with the grating, acts as a shutter. The shuttered light falling on a detector results in the generation of electrical signals. These signals are amplified and output as two amplified sinusoidal or square waves in quadrature and are output on two separate channels as signals SIN and COS. With simple incremental encoders, the position is measured by counting the zero crossings (sinusoidal) or edges (square waves) of both channels. Where greater precision is required, the amplified sinusoidal signals (SIN and COS) are sent to an encoder multiplier where the intermediate positions are resolved at spaced time intervals.

An encoder multiplier uses the SIN and COS signals to resolve many positions within one grating period (scribe lines). The multiplier, for example, is able to produce up to 65,000 transitions within one grating period as opposed to the four by a simple incremental encoder. See, for example, U.S. Pat. No. 6,356,219 entitled "Calibrated Encoder Multiplier". Feedback from the incremental encoders can be used to control the currents applied to each phase of the windings to precisely position the stages.

Having thus defined our invention in the detail and particularity required by the Patent Laws, what is desired protected by Letters Patent is set forth in the following claims.

The invention claimed is:

1. A laser machining apparatus based upon high precision z-theta stage having a horizontal translation axis (z-axis) and a rotary axis (theta-axis) parallel with the translation axis comprising:

a base plate having planar upper surfaces;

parallel spaced apart linear translation stages each having parallel linear bearings with bearing surfaces mounted in the same plane, each linear translation stage having a brushless linear motor;

a carriage supported between the parallel translation stages by the linear bearings; and a rotation stage carried by the carriage between the parallel translation stages, said rotation stage comprising a brushless rotary motor having a shaft journaled with a rotation axis parallel to the linear bearings, the carriage and rotation stage having a vertical and a horizontal center of gravity, each brushless linear motor being connected to the carriage to apply translation forces in a horizontal plane intersecting said vertical center of gravity, a laser optics centering stage mounted to the base plate for moving perpendicular to a given line intersecting an extension of the rotation axis of the rotary motor, a laser optics focusing mounted to the centering stage for moving toward and away from an extension the rotating axis of the rotary motor parallel to the given line intersecting the rotating axis of the motor, and laser optics mounted on said focusing stage.

2. A laser machining apparatus according to claim 1, wherein the centering stage moves along a tangent to a given circle included in a plane perpendicular to the axis of the rotary motor with its center at the axis and the focusing stage moves toward and away from the axis in a direction parallel to the radius of the given circle.

3. A laser machining apparatus according to claim 1, wherein the axis of the rotary motor is substantially horizontal, the centering stage moves substantially vertically and the focusing stage moves substantially horizontally, and the focusing stage moves toward and away from the axis of the rotary motor along a line intersecting the axis and included in a vertical plane.

4. The laser machining apparatus according to claim 1, wherein a linear position feedback means is associated with one brushless linear motor.

5. The laser machining apparatus according to claim 1, wherein a linear position feedback means is associated with each brushless linear motor.

6. The laser machining apparatus according to claim 1, wherein a rotary feedback means is associated with the brushless rotary motor.

7. The laser machining apparatus according to claim 1, having a fluid-actuated, workpiece-holding chuck or collet attached to the shaft of the rotary motor.

8. The laser machining apparatus according to claim 1, wherein the shaft of the rotary motor is hollow to permit a cylindrical workpiece and/or a fluid-cooling jacket to be positioned therein.

9. The laser machining apparatus according to claim 1, further comprising an auxiliary tooling platform for holding brackets for guiding and feeding a workpiece along the axis of the shaft of the rotary motor and being axially spaced therefrom.

10. The laser machining apparatus according to claim 1, wherein the parallel translation stages support two identical carriages facing each other, each carrying an identical rotation stage.

11. The laser machining apparatus according claim 1, wherein the horizontal center of gravity of the carriage and rotary stage is halfway between each linear motor.

12. The laser machining apparatus according to claim 1, wherein each linear stage contains a linear motion guide, cross roller bearing, or air bearing.

13. The laser machining apparatus according to claim 1, wherein each linear motor is connected to the carriage at multiple locations spaced in the direction of linear translation.

* * * * *

UNITED STATES PATENT AND TRADEMARK OFFICE
CERTIFICATE OF CORRECTION

| | | |
|---|---|---|
| PATENT NO. | : 7,038,334 B2 | Page 1 of 1 |
| APPLICATION NO. | : 11/069213 | |
| DATED | : May 2, 2006 | |
| INVENTOR(S) | : Botos et al. | |

It is certified that error appears in the above-identified patent and that said Letters Patent is hereby corrected as shown below:

<u>Column 6</u>, Line 32, "focusing mounted" should read -- focusing stage mounted --

Signed and Sealed this

First Day of August, 2006

JON W. DUDAS
*Director of the United States Patent and Trademark Office*